United States Patent [19]

Rebrovic et al.

[11] Patent Number: 5,231,192
[45] Date of Patent: Jul. 27, 1993

[54] PROCESS FOR THE PREPARATION OF ALPHA-ALKYL LACTONES

[75] Inventors: Louis Rebrovic, Cincinnati; Eugene G. Harris, West Chester, both of Ohio

[73] Assignee: Henkel Corporation, Ambler, Pa.

[21] Appl. No.: 619,797

[22] Filed: Nov. 29, 1990

Related U.S. Application Data

[63] Continuation-in-part of Ser. No. 402,105, Sep. 1, 1989, Pat. No. 4,980,342, which is a continuation-in-part of Ser. No. 315,109, Feb. 24, 1989.

[51] Int. Cl.$^5$ .................. C07D 309/18; C07D 307/28
[52] U.S. Cl. ..................................... 549/273; 549/295
[58] Field of Search ............................... 549/273, 295

[56] References Cited

U.S. PATENT DOCUMENTS 4,734,511  3/1988  Inagaki et al. ...................... 549/273
4,943,652  7/1990  Yatogai et al. ..................... 549/295

Primary Examiner—C. Warren Ivy
Assistant Examiner—A. A. Owens
Attorney, Agent, or Firm—Ernest G. Szoke; Wayne C. Jaeschke; Henry E. Millson, Jr.

[57] ABSTRACT

Process for the preparation of α-alkyl lactones by the steps of first reacting an α-acyl lactone, an aldehyde, and an alkali metal hydroxide together to form an α-alkylidene lactone, and then hydrogenating the α-alkylidene lactone.

28 Claims, No Drawings

PROCESS FOR THE PREPARATION OF ALPHA-ALKYL LACTONES

CROSS REFERENCE TO RELATED APPLICATIONS

This application is a continuation-in-part of application Ser. No. 07/402,105 filed on Sep. 1, 1989, now U.S. Pat. No. 4,980,342 which is in turn a continuation-in-part of application Ser. No. 07/315,109 filed on Feb. 24, 1989.

BACKGROUND OF THE INVENTION

1. Field of the Invention

The present invention is directed to an improved process for the preparation of α-alkyl-lactones. The process involves reacting an α-acyl lactone, an aldehyde and an alkali metal hydroxide in a suitable diluent to form the α-alkylidene lactone and then hydrogenating to obtain the corresponding α-alkyl-substituted product.

2. Description of the Prior Art There has been considerable interest in the preparation of α-alkylidene lactones and their saturated analogues, i.e. α-alkyl lactones. Various Y-butyrolactones having alkyl substituents in the α-position are reported to have flower- or fruit-like aromas.

Synthetic routes to the α-alkylidene-substituted products generally involve either (a) formation of the α-methylene or α-alkylidene lactone from acyclic precursors containing all of the desired functional groups via a ring closure reaction; or (b) conversion of an existing group at the α-position on a preformed lactone ring to the corresponding α-methylene or α-alkylidene group. The α-alkylidene derivative can then conveniently be hydrogenated to the corresponding α-alkyl lactone. The present invention is directed to a process wherein the hydrogen and acetyl groups present in the α-position of a lactone ring are first removed and replaced with an α-alkylidene moiety and the α-alkylidene group is then hydrogenated (reduced) to produce an α-alkyl-Y-butyrolactone or α-alkyl-δ-valerolactone.

Numerous methods for the synthesis of α-methylene lactones are discussed in the review articles of P. A. Greico (Synthesis 1975, 67) and N. Petragnani et al. (Synthesis 1986, 157). None of the reactions described in either reference, however, deal with the preparation of α-alkylidene lactones. In fact, there is only one mention of the reaction of an acetyl group which is substituted at the α-position. Ueno et al (Tetrahedron Lett. 1978, 3753) describe the reaction of α-acetyl-γ-butyrolactone with paraformaldehyde, lithium diisopropylamide in tetrahydrofuran to produce α-methylene-γ-butyrolactone.

Ksander et al in J. Org. Chem. 1977, 42, 1180 describe the preparation of α-alkylidene lactones by the reaction of ethyl oxalylbutyrolactones, with an aldehyde in the presence of aqueous sodium hydroxide. There is no suggestion by Ksander et al to the use of αacyl-substituted lactones of any type for the reaction.

Ono et al (J. Org. Chem. 1983, 48, 3678) report the conversion of an ester group which is substituted at the α-position on a γ-butyrolactone ring to an α-isopropylidene moiety. The complex multi-step process involves reaction of the carbanion of an α-carboethoxy-γ-butyrolactone and 2-chloro-2-nitropropane in the presence of a 150-watt tungsten lamp followed by the addition of sodium bromide and heat. In the only situation where Ono et al utilize a ring structure having an acetyl group in the α-position, namely, 2-acetylcyclopentanone, the corresponding α-isopropylidene cyclopentanone is not produced.

A multi-step synthesis which involves formylating an α-lactone using sodium hydride and ethyl formate and then condensing the resulting enolate with an aldehyde to obtain the corresponding α-methylene-γ-lactone is reported by Murray et al in J.Chem.Soc., Chem, Commun., 1984 at pp. 132–133.

Various procedures for hydrogenating unsaturated hydrocarbon substituents on lactone or other ring systems are known. It would be highly useful if a process were available wherein the acyl substituent on a lactone could be readily replaced by an alkylidene moiety which in turn could be hydrogenated to produce the corresponding alkyl-substituted lactone. These and other advantages are realized with the process of the present invention which will be described in more detail to follow.

SUMMARY OF THE INVENTION

The present invention is directed to an improved process for the preparation of α-alkyl-γ-butyrolactones and α-alkyl-δ-valerolactones. In general, the process involves reacting an α-acyl lactone, an aldehyde and an alkali metal hydroxide in an inert diluent at a temperature in the range of from about 50° C. to about 150° C. while removing water of reaction to form the corresponding α-alkylidene lactone and then hydrogenating to obtain the α-alkyl lactone. The diluent used in the reaction to produce the α-alkylidene derivative is preferably one which forms an azeotrope with water boiling in the range of from about 50° C. to about 95° C. The diluent is typically utilized at a volume ratio (diluent: total reactant charge) of from about 1:1 to about 20:1. In one especially useful embodiment of the invention the α-acyl lactone and alkali metal hydroxide are combined and reacted prior to the addition of the aldehyde. When using this method the aldehyde is generally added after about 60% to 75% of the theoretical amount of water has been removed from the reaction mixture.

α-Acyl lactones utilized in the process can contain one or more hydrocarbon radicals having from 1 to 20 carbon atoms on the ring. The hydrocarbon radicals can be alkyl, cycloalkyl, aryl or substituted aryl groups. If more than one hydrocarbon substituent is present the total number of carbon atoms of the combined substituents typically does not exceed about 20. Acetyl is a preferred acyl moiety. The aldehydes will correspond to the formula R'CHO where R' is a hydrogen or a hydrocarbon radical having from 1 to 20 carbon atoms and the alkali metal hydroxide can be sodium hydroxide, which is preferred, potassium hydroxide or lithium hydroxide. Benzene, toluene, xylene and cyclohexane are particularly useful diluents for conducting the reaction.

The alkylidene group is hydrogenated to the corresponding alkyl moiety utilizing conventional hydrogenation procedures. The hydrogenation catalyst and conditions used are selected so that they do not reduce the carbonyl moiety or effect ring opening. In general, the hydrogenation is carried out at from about 1 to about 30 atmospheres hydrogen at a temperature from about 0° C. up to about 120° C. An inert solvent can be used for the hydrogenation. Heterogeneous supported catalysts of platinum, palladium, nickel and ruthenium are preferred; however, homogeneous catalysts can also be used. Palladium and platinum on carbon, calcium carbonate or barium sulfate are particularly useful. The amount of the metal on the support will generally range from about 1 to about 15 weight percent and these catalysts are generally employed at levels from about 0.025 to about 10 weight percent, based on the α-alkylidene lactone.

DETAILED DESCRIPTION

The present invention relates to a process for converting α-acyl-substituted lactones to α-alkyl-substituted lactones. The α-alkyl substituents include methyl, n-alkyl and branched-chain alkyl groups, or alkyl groups which are substituted with cycloalkyl or aryl moieties and similar groups. The butyrolactone derivatives of the invention can also be named as furanones. For example, the α-acetyl-, α-alkylidene-, and α-alkyl-substituted γ-butyrolactones would respectively be 3-acetyldihydro-2(3H)-furanone, 3-alkylidenedihydro-2(3H)-furanone, 3-alkyldihydro-2(3H)-furanone. The furanone nomenclature is particularly useful when designating compounds which have multiple substituents on the ring and is employed herein.

The reaction to obtain the α-alkylidene lactone involves reacting an α-acyl lactone, an aldehyde and an alkali metal hydroxide. The reaction is typically carried out in an inert diluent medium. The process is adaptable for use with any 5-or 6-membered lactone having an acyl moiety substituted at the α-position on the ring. The other ring positions can be unsubstituted or substituted with one or more hydrocarbon groups. α-Acyl lactones useful in the process will correspond to the general formulae

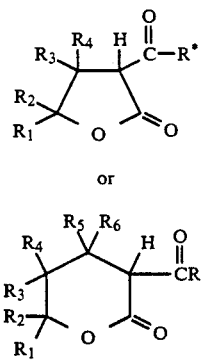

wherein $R^*$ is a $C_{1-8}$ alkyl group and $R_1$, $R_2$, $R_3$, $R_4$, $R_5$ and $R_6$ are, independently, selected from the group consisting of hydrogen or a hydrocarbon radical having from 1 to 20 carbon atoms. The hydrocarbon radicals can be alkyl, cycloalkyl, aryl or substituted-aryl groups. The process is, however, not dependent on the selection of any particular substituents. Generally, when more than one hydrocarbon group is present on the lactone ring the total number of carbon atoms of the combined hydrocarbon substituents will not exceed twenty (20). Particularly useful hydrocarbon radicals include $C_{1-8}$ alkyl, $C_{3-6}$ cycloalkyl, phenyl, $C_{1-8}$ alkyl-substituted phenyl, benzyl and $C_{1-8}$ alkyl-substituted benzyl. In one especially useful embodiment of the invention, the lactone corresponds to formula I, $R^*$ is $C_{1-4}$ alkyl and $R_1$, $R_2$, $R_3$ and $R_4$ are hydrogen or $C_{1-8}$ alkyl. In an even more preferred embodiment, $R^*$ is methyl $R_1$ is $C_{1-8}$ alkyl and $R_2$, $R_3$, and $R_4$ are hydrogen.

In another especially useful embodiment, the lactone corresponds to formula II, $R^*$ is $C_{1-4}$ alkyl and $R_1$, $R_2$, $R_3$, $R_4$, $R_5$ and $R_6$ are hydrogen or $C_{1-8}$ alkyl. In an even more preferred embodiment, $R^*$ is methyl, $R_1$ is $C_{1-8}$ alkyl and $R_2$, $R_3$, $R_4$, $R_5$ and $R_6$ are hydrogen.

Aldehydes employed in the process correspond to the general formula R'-CHO where R' is hydrogen or a hydrocarbon radical having from about 1 to 20 carbon atoms. The hydrocarbon group can be an alkyl, cycloalkyl, aryl or substituted-aryl group as previously defined for the lactone, and here again the process is not dependent on the selection of a particular R' group. When formaldehyde is the aldehyde of choice, paraformaldehyde is advantageously employed in the process as the formaldehyde source. The choice of aldehyde will dictate the nature of the α-alkylidene substituent. For example, when the α-acyl lactone corresponds to formula I, the resulting α-alkylidene-γ-butyrolactone will have the formula

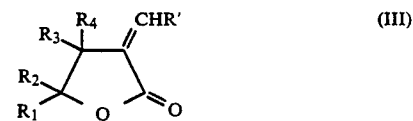

where $R_1$, $R_2$, $R_3$, $R_4$, $R_5$, $R_6$ and R' are the same as previously defined. When the α-acyl lactone corresponds to formula II, the resulting α-alkylidene-δ-valerolactone has the formula

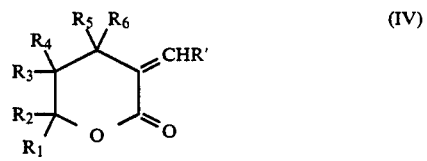

where $R_1$ $R_2$, $R_3$, $R_4$, $R_5$, $R_6$ and R' are the same as previously defined. In a particularly useful embodiment of the invention, the R' radical of the aldehyde and of the corresponding α-alkylidene lactone is hydrogen, a $C_{1-8}$ alkyl or alkenyl, $C_{3-8}$ cycloalkyl or cycloalkenyl, phenyl, substituted phenyl, benzyl, or substituted benzyl. Substituents that can be present on the phenyl or benzyl groups include $C_{1-8}$ alkyl, nitro, halo (Cl or Br), hydroxyl, carboxyl and carboalkoxy.

An alkali metal hydroxide is necessarily utilized with the α-acyl lactone and aldehyde for the reaction. Suitable alkali metal hydroxides include sodium hydroxide, potassium hydroxide and lithium hydroxide. The alkali metal hydroxide can be used as such or added as an aqueous solution. While it is not necessary to add water with the reactants, the presence of some water in the reaction mixture is generally considered to be advantageous. Since the alkali metal hydroxides are hygroscopic, there is generally sufficient water associated with these materials for the reaction. Also, as the reaction proceeds, additional water is produced. However, if the alkali metal hydroxide is added as an aqueous solution, the amount of water used will be such that it will not exceed 50%, by volume, of the reaction mixture. More typically, if water is added it constitutes from about 1% to 25%, by volume, of the reaction mixture.

The reaction is carried out at a temperature in the range 50° C. to 150° C. using an inert diluent as the reaction medium. Any diluent which is a liquid under the conditions employed for the reaction and which is substantially inert under the reaction conditions can be employed. Illustrative diluents include benzene, toluene, xylene, pentane, hexane, heptane, octane, isooctane, cyclohexane, ethylbutyl ether, diethyl acetal, dipropyl acetal, dibutyl acetal and the like. Inert diluents which form an azeotrope with water are particularly advantageous. Inert diluents which form an azeotrope boiling in the range 50° C. to 95° C. are particularly useful. The volume ratio of diluent to reactants can range from about 1:1 to 20:1 but most generally ranges from 2:1 to 8:1. Benzene, toluene, xylene and cyclohexane are especially advantageous diluents for the reaction in view of their azeotroping ability and availability.

The manner of adding the reactants is not critical. All of the reactants can be combined at the outset of the reaction, or as is more generally the case, two of the reactants can be combined and the remaining reactant added continuously or incrementally. For example, the alkali metal hydroxide can be added to a mixture of the $\alpha$-acyl lactone and aldehyde. In a particularly useful embodiment, the $\alpha$-acyl lactone and alkali metal hydroxide are combined and at least partially reacted prior to addition of the aldehyde to the mixture. This prereaction is conveniently accomplished by refluxing the $\alpha$-acetyl lactone and alkali metal hydroxide in a suitable diluent while removing water. The refluxing and azeotropic removal of water is typically carried out at a temperature in the range 50° C. to 95° C. When the distillation slows, usually when about 60% to 75% of the theoretical amount of water has been removed, the aldehyde is then added and the mixture is heated at reflux until essentially all of the water formed during the reaction is removed. As the water is removed, the temperature of the reaction increases to the maximum possible with the particular diluent being used. The temperature of the reaction mixture is generally maintained at about 75° C. to 125° C. during this stage of the reaction. If desired, the reaction temperature can be increased by distilling off the original diluent and adding a higher boiling inert solvent.

Essentially equimolar amounts of the reactants are preferably employed to optimize the yields of the $\alpha$-alkylidene lactone. A slight molar excess, generally not exceeding 20% and, more preferably, less than 10% can be used for the lactone or the aldehyde and may be advantageous depending on the method of combining the reactants. For example, when the $\alpha$-acyl lactone and alkali metal hydroxide are prereacted, a 10% to 15% molar excess of the aldehyde is often desirable.

The alkylidene moiety present at the $\alpha$-position of the lactone ring is hydrogenated using conventional hydrogenation procedures which selectively reduce the alkylidene group. Such conditions will be chosen by one skilled in the art so that the carbonyl group is not reduced and the lactone ring is not opened. The catalyst and conditions employed for the hydrogenation are selected so that only the unsaturation of the alkylidene group is reduced.

The hydrogenation can be carried out using either heterogeneous or homogeneous catalysts. Hydrogen pressures can range from one atmosphere up to about 30 atmospheres. While it is not necessary, the hydrogenation can be conducted in an inert solvent. The hydrogenation can be carried out at temperatures ranging from about 0° C. up to about 120° C. Most generally, however, the temperature will range form 25° C. up to about 85° C. Illustrative solvents which can be used include methanol, ethanol, propanol, isopropanol, n-butanol, t-butanol, octanol, 2-ethylhexanol, toluene, benzene, xylene, acetonitrile, dimethyl formamide, tetrahydrofuran, diethyl ether and the like. The solvent can be the same as employed for the reaction of the $\alpha$-acyl lactone, alkali metal hydroxide and aldehyde in which case, the $\alpha$-alkylidene lactone product may be directly hydrogenated without isolation, i.e., removal of the solvent. If desired, however, the $\alpha$-alkylidene lactone can be isolated prior to hydrogenation. The crude product can be hydrogenated or the $\alpha$-alkylidene lactone can be purified.

Heterogeneous catalysts are preferably used and include supported palladium, platinum, nickel and rhodium catalysts wherein the metal is present on the support in an amount from to 15 weight percent and more preferably, from 2 to 10 weight percent. Preferred catalysts include palladium on carbon, palladium on calcium carbonate, palladium on barium sulfate, platinum on carbon, platinum on calcium carbonate, and platinum on barium sulfate. Other useful catalysts include platinum oxide, palladium oxide, platinum black, nickel on alumina, nickel on kieselguhr, Raney nickel, rhodium on aluminum oxide and the like. The amount of supported metal catalyst used, based on the $\alpha$-alkylidene lactone, can range from 0.025 to 10 weight percent, based on the $\alpha$-alkylidene lactone, and, more preferably, from 0.05 to 5 weight percent. Homogeneous catalysts which can be used include tris(triphenylphosphine) rhodium chloride in $C_6H_6$-ETOH, dichlorotris (triphenylphosphine)ruthenium in $C_6H_6$ and tris(triphenylphosphine) rhodium chloride in the presence of triethysilane.

In general, upon completion of the hydrogenation the $\alpha$-alkyl lactone product is recovered after removal of the catalyst. When a heterogeneous catalyst is used, which is a preferred embodiment of the invention, this is typically accomplished by filtration or decantation. When a solvent is used for the hydrogenation, the solvent is generally evaporated to recover the product which can then be purified by distillation, recrystallization or the like. The $\alpha$-alkyl derivatives will correspond to the formulas

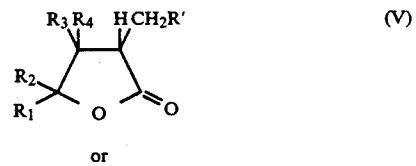

(V)

or

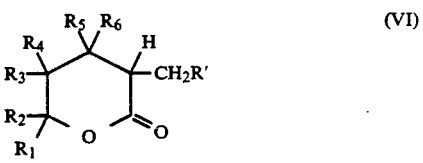

(VI)

where $R_1$, $R_2$, $R_3$, $R_4$, $R_5$, $R_6$, and $R'$ are the same as previously defined.

In cases where $R_1$ and $R_2$ are not both equal to an alkyl radical having from 1 to 20 carbon atoms, then $R_2$ must be hydrogen. This is because the hydrogenation has been found to be steroselective; that is, the cis isomer is the only isomer formed in any detectable amount.

This conclusion is based on the fact that the gas chromatographic analysis of the crude product mixture shows only one compound. $^{13}$C and $^1$H NMR spectra of the compound revealed that it is the cis isomer. The $^{13}$C NMR spectrum was compared to the cis and trans 3,5-dimethyl-2(3H)-furanone reported in J. Amer. Chem. Soc., 106, 1079 (1984). The cis stereochemistry was also deduced from the analysis of the $^1$H NMR spectrum with use of lathanide induced shift (LIS) data, specifically Eu(fod)$_3$. Accordingly, the invention also relates to a process for preparing a cis α-alkyl-γ-butyrolactone of formula VIII

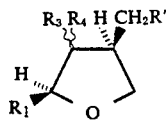

(VIII)

wherein R$_1$ is a hydrocarbon radical having from 1 to 20 carbon atoms, and R$_3$, R$_4$ and R' are independently hydrogen or a hydrocarbon radical having from 1 to 20 carbon atoms comprising the steps of: (A) reacting together (a) an acyl lactone of formula IX

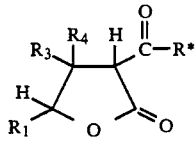

(IX)

wherein R$_1$, R$_3$, and R$_4$ have the meanings given above, and R* is a C$_{1-8}$ alkyl group, (b) an aldehyde of the formula R$^1$-CHO wherein R$^1$ is hydrogen or a hydrocarbon radical having from 1 to 20 carbon atoms, and (c) an alkali metal hydroxide at a temperature of from about 50° C. to about 150° C. in an inert diluent while removing water of reaction to form an α-alkylidene-γ-butyrolactone; and (B) hydrogenating said α-alkylidene-γ-butyrolactone under conditions which selectively reduce the alkylidene group of said α-alkylidene-γ-butyrolactone to form a cis α-alkyl-γ-butyrolactone.

It is preferred that R$_1$, and when either or both of R$_3$ and R$_4$ are hydrocarbon radicals, be either C$_{1-8}$ alkyl, C$_{3-6}$ cycloalkyl, phenyl, C$_{1-8}$ alkyl-substituted phenyl, benzyl, or C$_{1-8}$ alkyl-substituted benzyl.

Particularly preferred groups are where R* is C$_{1-4}$ alkyl, R$_1$ is C$_{1-8}$ alkyl, R$_3$ and R$_4$ are hydrogen or C$_{1-8}$ alkyl, and R' is hydrogen, C$_{1-8}$ alkyl or alkenyl, C$_{3-8}$ cycloalkyl or cycloalkenyl, phenyl or substituted phenyl, or benzyl or substituted benzyl.

It is especially preferred for compounds of formula VIII where R$_3$ and R$_4$ are hydrogen and R$_1$ and —CH$_2$R' are independently each a C$_1$-C$_7$ alkyl radical.

The present invention further relates to a process for the preparation of a cis α-alkyl-δ valerolactone of formula X

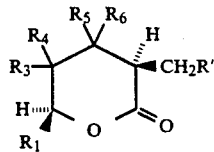

(X)

wherein R$_1$ is a hydrocarbon radical having from 1 to 20 carbon atoms, and R$_3$, R$_4$, R$_5$, R$_6$ and R' are hydrogen or a hydrocarbon radical having from 1 to 20 carbon atoms, comprising the steps of (A) reacting at a temperature in the range of from about 50° C. to about 150° C. and in an inert diluent while removing water of reaction (a) an α-acyl lactone of formula XI

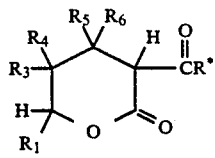

(XI)

wherein R$_1$, R$_3$, R$_4$, R$_5$ and R$_6$ have the meaning given above and R* is a C$_{1-8}$ alkyl group, (b) an aldehyde of the formula R'CHO where R' is hydrogen or a hydrocarbon radical having from 1-20 carbon atoms, and (c) an alkali metal hydroxide; and (B) hydrogenating the product obtained from step (A) under conditions which do not reduce the carbonyl group or effect ring opening to form a cis α-alkyl-δ-valerolactone.

Preferred substituents for the above reaction are wherein R* is C$_{1-4}$ alkyl, R$_1$ is a C$_{1-8}$ alkyl, R$_3$, R$_4$, R$_5$, and R$_6$ are hydrogen or C$_{1-8}$ alkyl and R' is hydrogen C$_{1-8}$ alkyl or alkenyl, C$_{3-8}$ cycloalkyl or cycloalkenyl, phenyl or substituted phenyl, or benzyl or substituted benzyl.

It is particularly preferred where R$_3$, R$_4$, R$_5$ and R$_6$ are all hydrogen.

All of the compounds made by the process of the present invention can be used as aroma chemicals in fragrances. The cis isomers of 3,5-dialkyl-dihydro-2(3H)-furanones made by the process of the present invention are particularly useful as aroma chemicals in a variety of applications. A fragrance can be defined as a mixture of natural and/or synthetic materials which impart fragrance or aroma to another substance. Fragrances are used to impart odors to such substances as perfumes, colognes, and perfumed articles of all types such as cosmetics, room deodorizers, fabric softeners, laundry cleaning products, sanitary paper products, and candles just to name a few. Compounds that are used in fragrances include plant materials such as essential oils, flower oils, resins, animal secretions, isolates from plant materials, derivatives of plant materials, and aroma chemicals. The amount of fragrance used to impart odor to a substance varies. For example, perfume typically contains from about 15% to about 30% by weight of fragrance. Aroma chemicals are compounds which enhance or augment the characteristic odor of a fragrance. Aroma chemicals are usually single compounds with known structures as opposed to the other fragrance ingredients such as essential oils, flower oils, and animal secretions. Aroma chemicals are well known in the art of perfumery. Examples of aroma chemicals include but are not limited to benzyl acetate which exhibits a characteristic floral odor type, citronellol which exhibits characteristic rosy and citrus odor types, geraniol which exhibits characteristic floral, rose and geranium odor types, and isobornyl acetate which exhibits a characteristic pine needle odor type. When one or more aroma chemicals are added to a fragrance, a certain odor is enhanced or made more prominent. For example, U.S. Pat. No. 4,824,828 discloses the use of certain types of schiff bases in an aroma-enhancing process. Specifically, the inclusion of the schiff base of methyl anthranilate imparts a lemony undertone to a floral fragrance disclosed in Example X of the patent.

When the present compounds, e.g. the cis-3,5-dialkyl-dihydro-2(3H)-furanones, made by the process of the present invention are incorporated into a fragrance, they enhance or augment the odor of those fragrances. For example, the inclusion of about 5% by weight of cis-3-methyl-5-butyl-dihydro-2(3H)-furanone into a fragrance exhibiting a slight citrus-type odor enhances or heightens the citrus odor. It will be appreciated that the type of odor augmentation depends upon the nature of the fragrance and the amount of the compounds added. Typically, the amount of the compounds of the invention, e.g. cis-3,5-dialkyl-dihydro-2(3H)-furanones, added to a fragrance will fall in the range of from about 0.01% to about 30% by weight. The preferred range is from about 0.5% to about 25% by weight. Any of the cis-3,5-dialkyl-dihydro-2(3H)-furanones of the formula VII

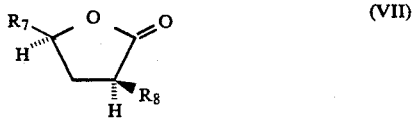

(VII)

wherein $R_7$ and $R_8$ are independently each $C_1$-$C_7$ alkyl radicals, can be used and are preferred for use as aroma chemicals to augment or enhance the odor of a fragrance. The particularly preferred compounds are cis-3-methyl-5-butyl-dihydro-2(3H)-furanone, cis-3-methyl-5-propyldihydro-2(3H)-furanone, cis-3-propyl-5-butyl-dihydro-2(3H)-furanone, and cis-3-heptyl-5-methyl-2(3H)-furanone.

Table I lists the particularly preferred cis-3,5-dialkyl-dihydro-2(3H)-furanones of the formula VII and their odor types.

TABLE I

| Compound | Odor Type |
|---|---|
| A. cis-3-methyl-5-propyldihydro-2(3H)-furanone | strong, coumarenic |
| B. cis-3-methyl-5-butyl-dihydro-2(3H)-furanone | oak, maple, nutty |
| C. cis-3-heptyl-5-methyl-dihydro-2(3H)-furanone | nutty, pecan |
| D. cis-3-propyl-5-butyl-dihydro-2(3H)-furanone | nutty, walnut |

The following examples illustrate the invention more fully but are not intended as a limitation on the scope thereof. In these examples all parts and percentages are given on a weight basis unless otherwise indicated.

EXAMPLE

Preparation of α-Acetyl Lactone

Sodium hydroxide (100 g/400 g water) was charged to a one liter, four-neck flask equipped with an ice bath, mechanical stirrer, dry ice condenser, pot thermometer and addition funnel. Ethyl acetoacetate (325 g, 2.5 moles) and propylene oxide (174 g, 3.0 moles) were mixed and charged to the addition funnel. The pot was cooled to 15° C. and the ethyl acetoacetate-propylene oxide mixture was added below 20° C. over a period of two hours. The reaction mixture was then stirred for six hours and transferred to a separatory funnel and acidified with 225 ml of concentrated hydrochloric acid. The two layers were separated and the lower aqueous layer extracted three times with diethyl ether. The combined extracts were dried over sodium sulfate and the diethyl ether removed using a Rotovap at 70° C. (aspirator pressure). The resulting product was distilled using a packed column and a Perkins Triangle Head. Fractions 1-3 (94 g) contained mostly ethyl acetoacetate. A fourth fraction (170 g) boiling point at 112°-117° C. at 7 torr contained essentially 100% of the desired α-acetyl lactone, 3-acetyl-5-methyldihydro-2(3H)-furanone.

Conversion of the α-Acetyl Lactone to α-Alkylidene Lactone

3-Acetyl-5-methyldihydro-2(3H)-furanone 28.4 g 0.200 mole) was combined with 200 ml toluene in a 500 ml flask fitted with a mechanical stirrer, a Dean-Stark trap and an addition funnel. Eight grams (0.200 mole) of sodium hydroxide was added and the mixture stirred at room temperature for 10 minutes and then heated under reflux for one hour during which time water was removed in the Dean-Stark trap. Cyclohexanecarboxaldehyde (25.7 g; 0.225 mole) was then slowly dripped into the reaction mixture over a period of approximately one hour. The mixture was heated under reflux for another four hours and the reaction mixture then cooled to room temperature and washed three times with 100 ml of $H_2O$ and dried over $Na_2SO_4$. Filtration followed by evaporation of the toluene solvent yielded 35 g of the crude α-alkylidene lactone product, 3-cyclohexyl-methylene-5-methyldihydro-2(3H)-furanone. The crude product was distilled under vacuum using a 1×20 cm Vigreaux column to obtain 20.8 g 3-cyclohexyl-methylene-5-methyldihydro-2(3H)-furanone (94% assay by GLC, 50% yield, boiling range 105°-134° C. at 0.20 mm of Hg). The structure of the product was confirmed by proton and carbon nuclear magnetic resonance spectroscopy:

$^1$HNMR(CDCL$_3$): δ6.57 (m,0.37H), 6.0 (m, 0.63H), 4.6(m,1H) 3.44 m,0.53), 3.1(m,1H), 2.44 (m,1H) 2.19 (m,0.47H), 1.87-0.9 (series of complex multiplets 13H).
$^{13}$CNMR(CDCL$_3$) δ171.309, 170,148.981, 145.260, 124.788, 23.087, 73.990, 73.696, 39.393, 36.870, 35.766, 32.726, 32.550, 32.441, 31.515, 31.434, 25.869, 25.738, 25.396, 22.223, 21.775.

GLC analysis showed the product to be comprised of 66.7% Z isomer and 33.3% E isomer.

Hydrogenation of α-Alkylidene Lactone to α-Alkyl Lactone

3-Cyclohexylmethylene-5-methyldihydro-2(3H)-furanone (6 g; 0.031 moles) was charged with 0.5 g 5% platinum on carbon catalyst and 8 ml ethanol to a 25 ml flask equipped with a magnetic stirring bar and capped with a rubber septum. A syringe needle which extended through the septum to below the surface of the reaction mixture was provided for introducing the hydrogen. The reaction vessel was also fitted with a second syringe needle extending through the septum to above the surface of the mixture and connected to an oil bubbler. The mixture was stirred at room temperature and hydrogen introduced at a moderate rate for 15 hours. The mixture was then filtered through diatomaceous earth to remove the catalyst. The ethanol was removed under reduced pressure to recover 6.1 g (99% yield) cis-3-cyclohexylmethyl-5-methyldihydro-2(3H)-furanone.

The material crystallized upon standing and was recrystallized from 1:1 ethanol/water to obtain essentially pure product which melted at 68°-69° C. The structure of the product was confirmed by proton nuclear resonance spectroscopy.

¹HNMR(CDCl₃) δ4.48(m,1H), 2.6(m,2H), 2.0–0.75(series of complex multiplets with doublet at 1.4, 17H).

EXAMPLE II

To demonstrate the versatility of the process and the ability to obtain lactones having an n-alkylidene moiety in the α-position, Example I was repeated except that heptaldehyde was substituted for the cyclohexanecarboxaldehyde. Upon distillation of the reaction mixture, 3-heptylidene-5-methyldihydro-2(3H)-furanone was recovered in 54.5% yield (boiling range 113°–120° C. at 0.05 mm of Hg). The structure of the product was confirmed by proton nuclear magnetic resonance:

¹HNMR (CDCL₃): δ6.55 (m, 0.66H), 6.04(m, 0.34H), 4.5(m, 1H) 3.0–1.85 (series of complex multiplets, 4H) 1.44–1.0 (multiplet with triplet at 1.25, 11H), 0.75 (distorted triplet, 3H).

When the reaction was repeated using potassium hydroxide as the base, the reaction proceeded without difficulty although at a somewhat slower rate to produce 3-heptylidene-5-methylidhydro-2(3H)-furanone.

Using the same general hydrogenation procedure described in Example I, 3-heptylidene-5-methyldihydro-2(3H)-furanone (10 g; 0.051 mole) was combined with 0.5 g 5% palladium on carbon catalyst and 10 ml ethanol. Hydrogen gas was bubbled into the mixture over a 12 hour period with stirring. After removal of the catalyst and evaporation of the solvent, 9.95 g (96% assay by GLC; 95% yield) cis-3-heptyl-5-methyldihydro-2(3H)-furanone was recovered. The proton nuclear resonance spectrum for the product was as follows:

¹HNMR(CDCl₃): δ4.47(m,1H), 2.53(m,2H), 2.0–1.1 (series) of multiplets with doublet at 1.42, 16H), 0.89 (t,3H)

EXAMPLE III

Example I was repeated using heptaldehyde, 3-acetyl-5-ethyldihydro-2(3H)-furanone and sodium hydroxide to obtain the corresponding α-alkylidene-δ-butyrolactone. The product, 3-heptylidene-5-ethyldihydro-2(3H)-furanone, boiled in t 13°–118° C. (0.06 mm/Hg) and had the following proton nuclear magnetic resonance spectrum:

¹HNMR (CDCl₃): δ6.7(tt,0.42H), 6.2(tt, 0.58H), 4.42(m,1H) 3.1–0.8 (series of complex multiplets 20H)

The product prepared above was hydrogenated following the general procedure described in Example I. For the reaction, 2.1g 3-heptylidene-5-ethyldihydro-2(3H)-furanone (0.010 mole) was combined with 0.1 g 5% palladium on carbon and 5 ml ethanol and hydrogen gas slowly introduced for 1.5 hours. Upon removal of the catalyst and evaporation of the solvent, 2.0 g (97% assay by GLC; 95% yield)

3-heptyl-5-ethyldihydro-2(3H)-furanone was recovered.

¹HNMR(CDCl₃): δ4.28(m,1H), 2.5(m,2H), 2.0–1.1(series of complex multiplets, 14H), 1.0 and 0.89 (two triplets, 6H)

EXAMPLE IV

To demonstrate the ability to prepare an α-methylene-γ-butyrolactone, 3-acetyl-5-butyldihydro-2(3H)-furanone was reacted with sodium hydroxide and paraformaldehyde in accordance with the procedure of Example I.

3-Methylene-5-butyldihydro-2(3H)-furanone boiling at 87° C. (0.2 mm/Hg) was obtained in 70% yield. Proton and carbon nuclear magnetic resonance spectra for the product were as follows:

¹HNMR (CDCl₃): δ6.2 (very closely spaced triplet, 1H), 5.64 (very closely spaced triplet, 1H), 4.55 (pentet, 1H), 3.1 (m, 1H), 2.6 (m, 1H), 1.9–1.15 (m, 6H), 0.91 (t, 3H) ¹³CNMR (CDCl₃): δ170.368, 134.993, 121.712, 77.656, 35.979, 33.550, 26.999, 22.414, 13.919.

3-Methylene-5-butyldihydro-2(3H)-furanone (5.8 g; 0.33 mole) was charged to a reactor with 0.25 g 5% palladium on carbon and 6 mls ethanol. The mixture was stirred at room temperature and hydrogen gas slowly introduced subsurfacely for eight hours. The catalyst was removed by filtering and the solvent evaporated under reduced pressure to yield 5.3 g of cis-3-methyl-5-butyldihydro-2(3H) furanone (84% assay by GLC;86.5% yield)

¹HNMR(CDCl₃): δ4.34(m,1H), 2.6(m,2H), 1.9–1.1(series of complex multiplets with a doublet at 1.25, 10H), 0.9(t,3H).

¹³CNMR(CDCl₃): δ179.6, 78.7, 37.4, 35.9, 35.2, 27.4, 22.5, 15.1, 13.9.

EXAMPLE V

3-Phenylmethylene-5-butyldihydro-2(3H)-furanone was prepared by reacting 3-acetyl-5-butyldihydro-2(3H)-furanone with sodium hydroxide and benzaldehyde in accordance with the procedure described in Example I. The crude product (64.5% yield) was recovered by distillation of the reaction mixture at 25°–147° C. (0.04 mm/Hg) to remove light ends. The structure was confirmed by proton nuclear magnetic resonance spectroscopy.

¹HNMR (CDCl₃): δ7.5 (m,6H), 4.56 (pentet,1H),3.3 (ddd,1H) 2.8 (ddd, 1H) 1.9–1.2 (m,6H), 0.86(t,3H)

The reaction was repeated using 3-acetyl-dihydro-2(3H)-furanone, sodium hydroxide and benzaldehyde to produce 3-phenyl methylene-dihydro-2(3H)-furanone. The crude yellow solid obtained from the reaction was recrystallized from chloroform to recover 3-phenylmethylene-dihydro-2(3H)-furanone, a yellow crystalline solid melting at 116° C. Proton and carbon nuclear magnetic resonance spectra for the product were as follows:

¹HNMR (CDCl₃): δ7.526(t,1H, J=3Hz), 7.45 (m,5H), 4.42(t,2H, J=7.6 Hz) 3.208 (dt, 2H, J=7.6, 3.0Hz)

¹³CNMR (CDCl₃): δ172.455, 136.414, 134.598, 129,963, 129.805, 128.904, 123.685, 65.447, 27.368

3-Phenylmethylene-5-butyldihydro-2(3H)-furanone (5.95 g 0.026 mole) was combined with 0.28 g 5% palladium on carbon and 8 mls ethanol and hydrogenated for eight hours as in Example 1. Upon removal of the catalyst and solvent, 6.0 g 3- benzyl-5-butyldihydro-2(3H)-furanone was recovered. The structure of the product was confirmed by proton magnetic resonance spectroscopy.

¹HNMR(CDCl₃): δ7.25(m,5H), 4.30(m,1H), 3.35–1.10 (series of complex multiplets, 11H), 0.83 (t, 3H).

EXAMPLES VI AND VII

Two reactions were carried out in accordance with the process of the invention using valeraldehyde. For one reaction (Example VI) 3-acetyl-dihydro-2(3H)-furanone was used and for the second reaction (Example VII) 3-acetyl-5-n-butyldihydro-2(3H)-furanone was employed. Both reactions used sodium hydroxide with toluene as the diluent and the reactants were present in essentially equimolar amounts. 3-Pentylidene-dihydro-2(3H)-furanone (86°-104° C. at 0.1 mm/Hg) and 3-pentylidene-5-n-butyldihydro-2(3H)-furanone (110°-131° C. at 0.01 mm/Hg) were obtained from the respective reactions. Proton nuclear magnetic resonance spectra for the products were as follows:

3-Pentylidene-dihydro-2(3H)-furanone:
$^1$HNMR (CDCl$_3$): δ6.7 (m, 0.93H), 6.26 (m, 0.07H), 4.4 (t, 2H), 2.9 (m, 2H), 2.22 (m, 2H), 1.4 (m, 4H), 0.9 (t, 3H).

3-Pentylidene-5-n-butyldihydro-2(3H)-furanone:
$^1$HNMR (CDCl$_3$): δ6.7 (tt, 0.4H), 6.2 (tt, 0.6H), 4.45 (m, 1H) 3.1-1.5 complex multiplets, 14H), 0.9 (two superimposed triplets, 6H).

Hydrogenation of the 3-pentylidene-5-n-butyldihydro-2(3H)-furanone yielded 3-pentyl-5-n-butyldihydro-2(3H)-furanone.

EXAMPLE VIII

2-Methylbutyraldehyde was reacted with 3-acetyl-5-ethyldihydro-2(3H)-furanone and sodium hydroxide to produce 3-(1-methylpropyl)methylene-5-ethyldihydro-2(3H)-furanone (88% assay by GLC). The product boiled in the range 80°-94° C. at 0.2 mm of Hg and had the following proton nuclear magnetic resonance spectrum:

$^1$HNMR(CDCl$_3$): δ6  5(td,0.22H),5.92(td,0.78H), 4.4(m,1H),3.67-0.76 (series of complex multiplets, 16H)

Hydrogenation of the 3-(1-methylpropyl)methylene-5-ethyldihydro-2(3H)-furanone yielded 3-(2-methylbutyl)-5-ethyldihydro-2(3H)-furanone.

EXAMPLE IX

To further demonstrate the versatility of the process, the procedure of Example II was repeated except that for the first step of the reaction cyclohexane was employed as the diluent. After eight hours (total reaction time) the reaction was terminated and the crude product 3-heptylidene-5-methyldihydro-2(3H)-furanone was recovered in the usual manner (45.6% yield). Hydrogenation of the product yielded 3-heptyl-5-methyldihydro-2(3H)-furanone.

EXAMPLE X

Example I was repeated using propionaldehyde diethyl acetal as the azeotroping solvent for the reaction to produce the α-alkylidene lactone. For this experiment 100 ml propionaldehyde diethyl acetal was charged to the reactor with 14.9 g (0.10 mole) 3-acetyl-5-methyldihydro-2(3H)-furanone. The mixture was stirred and 4 g (0.10 mole) powdered sodium hydroxide added. The mixture was allowed to stir for 10 minutes and then heated to reflux for 5½ hours after which time 14.0 g (0.125 mole) cyclohexanecarboxaldehyde was added over a one-hour period. The mixture was heated under reflux for an additional twelve hours, cooled and worked up to recover 19 g crude 3-cyclohexylmethylene-5-methyldihydro-2(3H)-furanone (59% yield). The structure of the product was confirmed by proton and carbon nuclear magnetic resonance spectroscopy.

Hydrogenation of the product to produce the corresponding α-alkyl lactone can be carried out in accordance with the procedure of Example I.

EXAMPLE XI p-Nitrobenzaldehyde was reacted with 3-acetyl-5-butyldihydro-2(3H)-furanone. For the reaction, 9.21 g (0.05 mole) of the furanone and 7.55 g (0.05 mole) of p-nitrobenzaldehyde were combined with 2.5 g (0.065 mole) of sodium hydroxide in 25 ml water and 25 ml ethanol. A reaction occurred immediately. The light yellow solid was recovered by filtration and washed with ethanol. The product, 3-(p-nitrophenyl)methylene-5-butyldihydro-2(3H)-furanone, was confirmed by carbon nuclear magnetic resonance spectroscopy. Hydrogenation of the product in accordance with the procedure of Example 1 yielded 3-(p-nitrobenzyl)-5-butylidhydro-2(3H)-furanone.

EXAMPLE XII

To demonstrate the ability the ability to vary the hydrogenation procedure, 3-heptylidene-5-methyldihydro-2(3H)-furanone prepared following the general procedures of Example I was hydrogenated. For the reaction, crude 3-heptylidene-5-methyldihydro-2(3H)-furanone (650 g; 1.21 mole) was charged to a high-pressure Parr Stainless Steel autoclave with 0.055 g 5% palladium on carbon catalyst. The reactor was pressured with hydrogen to 400 psig and maintained at 85° C.-90° C. for 20 hours with agitation. Makeup hydrogen was added as necessary to maintain the pressure. At the completion of the reaction, the mixture was filtered to remove the catalyst and vacuum distilled. The fraction removed between 130° C.-147° C. (5 mm/Hg), which solidified upon cooling, was recrystallized from methanol/water to recover the 3-heptyl-5-methyldihydro-2(3H)-furanone (melting point 34.5° C.-35.5° C.).

EXAMPLE XIII

Effect of cis-3-methyl-5-butyl-dihydro-2(3H)-furanone on the Odor of a Fragrance

| Fragrance I[1] | | Fragrance II | |
|---|---|---|---|
| lemon oil | 26.3 | lemon oil | 25 |
| lime oil | 26.3 | lime oil | 25 |
| bergamot oil | 31.6 | bergamot oil | 30 |
| lavender oil | 42.2 | lavender oil | 40 |
| phenethyl alcohol | 105.3 | phenethyl alcohol | 100 |
| amyl cinnamaldehyde | 210.5 | amyl cinnamaldehyde | 200 |
| vertofix | 105.3 | vertofix | 100 |
| cedar wood oil | 52.6 | cedar wood oil | 50 |
| Texas patchouli oil | 21 | Texas patchouli oil | 20 |
| musk E.D. | 210.5 | musk E.D. | 200 |
| Compound B[2] | 50 | Compound B | — |

[1]-parts per thousand
[2]-Compound B (cis-3-methyl-5-butyl dihydro-2(3H) furanone)

We claim:

1. A process for preparing a cis α-alkyl-γ-butyrolactone of formula VIII

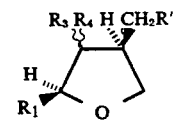

(VIII)

wherein R$_1$ is a hydrocarbon radical having from 1 to 20 carbon atoms, and R$_3$, R$_4$ and R' are independently hydrogen or a hydrocarbon radical having from 1 to 20 carbon atoms comprising the steps of:

(A) reacting together (a) an acyl lactone of formula IX

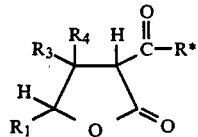

(IX)

wherein $R_1$, $R_3$, and $R_4$ have meanings given above, and $R^*$ is a $C_{1-8}$ alkyl group, (B) an aldehyde of the formula R—CHO wherein R is hydrogen or a hydrocarbon radical having from 1 to 20 carbon atoms, and (c) an alkali metal hydroxide at a temperature of from about 50° C. to about 150° C. in an inert diluent which is liquid under the conditions employed for the reaction and which is substantially inert under said reaction conditions while removing water of reaction to form an α-alkylidene-γ-butyrolactone; and (B) hydrogenating said α-alkylidene-γ-butyrolactone using a hydrogenation catalyst and conditions which selectively reduce the alkylidene group of said α-alkylidene-γ-butyrolactone to form a cis α-alkyl-γ-butyrolactone.

2. The process of claim 1 wherein the radicals $R_1$, $R_3$, and $R_4$ are selected from the group consisting of $C_{1-8}$ alkyl, $C_{3-6}$ cycloalkyl, phenyl, $C_{1-8}$ alkyl-substituted phenyl, benzyl and $C_{1-8}$ alkyl-substituted benzyl.

3. The process of claim 1 wherein $R^*$ is $C_{1-4}$ alkyl, $R_1$ is $C_{1-8}$ alkyl, $R_3$ and $R_4$ are hydrogen or $C_{1-8}$ alkyl, and $R'$ is hydrogen, $C_{1-8}$ alkyl or alkenyl, $C_{3-8}$ cycloalkyl or cycloalkenyl, phenyl or substituted phenyl, or benzyl or substituted benzyl.

4. The process of claim 1 wherein in step (A) components (a), (b), and (c) are present in substantially equimolar quantities.

5. The process of claim 1 wherein the hydrogenation is carried out at a pressure in the range of from about 1 to about 30 atmospheres and at a temperature of from about 0° C. to about 120° C. utilizing from about 0.025 to about 10 weight percent of a heterogeneous supported catalyst of platinum, palladium, nickel or ruthenium, said metal being present on the support in an amount of from about 1 to about 15 weight percent.

6. The process of claim 1 wherein the inert diluent of step (A) forms an azeotrope with water boiling in the range of from about 50° C. to about 95° C. and is present at a volume ratio of diluent: total reactant charge of about 1:1 to about 20:1.

7. The process of claim 5 wherein the hydrogenation is carried out in an inert diluent at a temperature of from about 25° C. to about 85° C.

8 The process of claim 1 wherein in step (A) the α-acyl lactone and alkali metal hydroxide are combined and reacted prior to addition of the aldehyde.

9. The process of claim 8 wherein the aldehyde is added after about 60% to 75% of the theoretical amount of water is removed.

10. The process of claim 8 wherein a molar excess of component (b) in step (A) is employed.

11. The process of claim 5 wherein the hydrogenation catalyst is a supported platinum or palladium catalyst wherein the metal is present on the support in an amount of from about 2 to about 10 weight percent.

12. The process of claim 1 wherein the same diluent is employed for steps (A) and (B) and is selected from the group consisting of benzene, toluene, xylene, and cyclohexane.

13. The process of claim 1 wherein $R_1$ and —$CH_2R'$ are independently each an alkyl radical having from 1 to 7 carbon atoms and $R_3$ and $R_4$ are hydrogen.

14. The process of claim 13 wherein $R_1$ is methyl and —$CH_2R'$ is butyl.

15. The process of claim 13 wherein $R_1$ is propyl and —$CH_2R'$ is butyl.

16. The process of claim 13 wherein $R_1$ is butyl and —$CH_2R'$ is propyl.

17. The process of claim 13 wherein $R_1$ is methyl and —$CH_2 R'$ is heptyl.

18. A process for the preparation of cis α-alkyl-δ-valerolactone of formula X

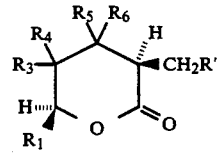

(X)

wherein $R_1$ is a hydrocarbon radical having from 1 to 20 carbon atoms, and $R_3$, $R_4$, $R_5$, $R_6$ and $R'$ are selected from the group consisting of hydrogen or a hydrocarbon radical having from 1 to 20 carbon atoms comprising the steps of:

(A) reacting at a temperature in the range of from about 50° C. to about 150° C. and in an inert diluent which is liquid under the conditions employed for the reaction and which is substantially inert under said reaction conditions while removing water of reaction (a) an α-acyl lactone of formula XI

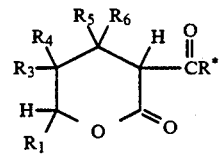

(XI)

wherein $R_1$, $R_3$, $R_4$, $R_5$ and $R_6$ have the meaning given above and $R^*$ is a $C_{1-8}$ alkyl group, (b) an aldehyde of the formula R'CHO where R' is hydrogen or a hydrocarbon radical having from 1–20 carbon atoms, and (e) an alkali metal hydroxide; and (B) hydrogenating the product obtained from step (A) using a hydrogenation catalyst and conditions which do not reduce the carbonyl group or effect ring opening to form a cis α-alkyl-δ-valerolactone.

19. The process of claim 18 wherein in step (A) components (a), (b), and (c) are present in substantially equimolar quantities.

20. The process of claim 18 wherein $R^*$ is $C_{1-4}$ alkyl, $R_1$ is a $C_{1-8}$ alkyl, $R_3$, $R_4$, $R_5$ and $R_6$ are hydrogen or $C_{1-8}$ alkyl and $R'$ is hydrogen, $C_{1-8}$ alkyl or alkenyl, $C_{3-8}$ cycloalkyl or cycloalkenyl, phenyl or substituted phenyl, or benzyl or substituted benzyl.

21. The process of claim 18 wherein the hydrogenation is carried out at a pressure in the range of from about 1 to about 30 atmospheres and at a temperature of from about 0° C. to about 120° C. utilizing from about 0.025 to about 10 weight percent of a heterogeneous supported catalyst of platinum, palladium, nickel or ruthenium, said metal being present on the support in an amount of from about 1 to about 15 weight percent.

22. The process of claim 18 wherein the inert diluent of step (A) forms an azeotrope with water boiling in the range of from about 50° C. to about 95° C. and is present at a volume ratio of diluent: total reactant charge of about 1:1 to about 20:1.

23. The process of claim 18 wherein the hydrogenation is carried out in an inert diluent at a temperature of from about 25° C. to about 85° C.

24. The process of claim 18 in step (A) the α-acyl lactone and alkali metal hydroxide are combined and reacted prior to addition of the aldehyde.

25. The process of claim 24 wherein the aldehyde is added after about 60% to 75% of the theoretical amount of water is removed.

26. The process of claim 24 wherein a molar excess of component (b) in step (A) is employed.

27. The process of claim 21 wherein the hydrogenation catalyst is a supported platinum or palladium catalyst wherein the metal is present on the support in an amount of from about 2 to about 10 weight percent.

28. The process of claim 18 wherein the same diluent is employed for steps (A) and (B) and is selected from the group consisting of benzene, toluene, xylene, and cyclohexane.

* * * * *